(12) United States Patent
Holm et al.

(10) Patent No.: US 9,457,123 B2
(45) Date of Patent: Oct. 4, 2016

(54) HYDROGELS WITH RELEASE ELEMENT

(75) Inventors: David R. Holm, Hudson, WI (US);
Scott A. Burton, Woodbury, MN (US);
Robert A. Asmus, Hudson, WI (US);
Richard L. Jacobson, Stillwater, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 13/119,225

(22) PCT Filed: Sep. 23, 2009

(86) PCT No.: PCT/US2009/057983
§ 371 (c)(1),
(2), (4) Date: Mar. 16, 2011

(87) PCT Pub. No.: WO2010/036682
PCT Pub. Date: Apr. 1, 2010

(65) Prior Publication Data
US 2011/0166492 A1    Jul. 7, 2011

Related U.S. Application Data

(60) Provisional application No. 61/099,584, filed on Sep. 24, 2008.

(51) Int. Cl.
*A61K 9/70* (2006.01)
*A61L 15/60* (2006.01)
*A61L 15/46* (2006.01)
*A61L 15/58* (2006.01)
*A61F 13/02* (2006.01)
*A61F 13/00* (2006.01)

(52) U.S. Cl.
CPC ............ *A61L 15/60* (2013.01); *A61F 13/0256* (2013.01); *A61L 15/46* (2013.01); *A61L 15/58* (2013.01); *A61F 2013/00753* (2013.01); *A61L 2300/404* (2013.01); *A61L 2300/602* (2013.01)

(58) Field of Classification Search
CPC .................................................... A61L 15/46
See application file for complete search history.

(56) References Cited

U.S. PATENT DOCUMENTS

| | | | |
|---|---|---|---|
| RE24,906 E | 12/1960 | Ulrich | |
| 3,389,827 A | 6/1968 | Abere | |
| 3,645,835 A | 2/1972 | Hodgson | |
| 4,112,213 A | 9/1978 | Waldman | |
| 4,310,509 A | 1/1982 | Berglund | |
| 4,323,557 A | 4/1982 | Rosso | |
| 4,366,814 A | 1/1983 | Riedel | |
| 4,472,480 A | 9/1984 | Olson | |
| 4,524,087 A | 6/1985 | Engel | |
| 4,737,410 A | 4/1988 | Kantner | |
| 4,867,742 A | 9/1989 | Calderon | |
| 4,867,748 A | 9/1989 | Samuelsen | |
| 4,909,244 A | 3/1990 | Quarfoot | |
| 4,931,282 A * | 6/1990 | Asmus et al. ............. | 424/78.06 |
| 5,059,424 A | 10/1991 | Cartmell | |
| 5,088,483 A | 2/1992 | Heinecke | |
| 5,106,629 A | 4/1992 | Cartmell | |
| 5,133,821 A | 7/1992 | Jensen | |
| 5,156,601 A | 10/1992 | Lorenz | |
| 5,160,315 A | 11/1992 | Heinecke | |
| 5,225,473 A | 7/1993 | Duan | |
| 5,270,358 A * | 12/1993 | Asmus ........................... | 524/55 |
| 5,276,079 A * | 1/1994 | Duan et al. .................... | 524/386 |
| 5,338,490 A * | 8/1994 | Dietz et al. .................... | 252/500 |
| 5,356,632 A | 10/1994 | Gross | |
| 5,389,376 A * | 2/1995 | Duan et al. .................... | 424/448 |
| 5,409,966 A * | 4/1995 | Duan et al. .................... | 522/152 |
| 5,423,737 A | 6/1995 | Cartmell | |
| 5,438,988 A * | 8/1995 | Duan et al. .................... | 600/391 |
| 5,447,492 A | 9/1995 | Cartmell | |
| 5,531,855 A | 7/1996 | Heinecke | |
| 5,714,225 A | 2/1998 | Hansen | |
| 5,849,325 A | 12/1998 | Heinecke | |
| 5,887,590 A | 3/1999 | Price | |
| 6,264,976 B1 | 7/2001 | Heinecke | |
| 6,436,432 B2 | 8/2002 | Heinecke | |
| 6,468,383 B2 | 10/2002 | Kundel | |
| 6,756,102 B1 | 6/2004 | Galo | |
| 6,838,589 B2 | 1/2005 | Liedtke | |
| 7,217,853 B2 | 5/2007 | Kulichikhin | |
| 2001/0031370 A1 | 10/2001 | Kundel | |
| 2003/0125680 A1 | 7/2003 | Ding | |
| 2004/0133143 A1 | 7/2004 | Burton | |
| 2004/0247654 A1 | 12/2004 | Asmus | |
| 2004/0247655 A1 | 12/2004 | Asmus | |
| 2005/0080372 A1 | 4/2005 | Nielsen | |
| 2006/0064049 A1 | 3/2006 | Marcussen | |

FOREIGN PATENT DOCUMENTS

| | | | |
|---|---|---|---|
| EP | 0424165 | * 10/1990 | ............. A61F 13/02 |
| EP | 0424165 | 4/1991 | |

(Continued)

OTHER PUBLICATIONS

International Search Report, PCT/US2009/057983, 3 pages.

*Primary Examiner* — Hasan Ahmed

(74) *Attorney, Agent, or Firm* — 3M Innovative Properties Company; Lynn R. Hunsberger

(57) ABSTRACT

An adhesive hydrogel dressing as well as methods of applying the dressing to a patient. The dressing generally comprises an adhesive hydrogel pad, a backing layer, and an adhesive layer on the backing layer facing the hydrogel pad. The adhesive layer and backing layer form a perimeter around the hydrogel pad and hold the hydrogel pad in place on an application surface. A release element is in contact with at least a portion of the edge of the hydrogel pad proximate the area that the hydrogel pad and release liner separate during liner removal.

18 Claims, 7 Drawing Sheets

(56) References Cited

FOREIGN PATENT DOCUMENTS

| | | |
|---|---|---|
| EP | 0919211 | 6/1999 |
| WO | WO 92/16245 | 10/1992 |
| WO | WO 94/12134 | 6/1994 |
| WO | WO 99-06077 | 2/1999 |
| WO | WO 02-20067 | 3/2002 |
| WO | WO0220067 * 3/2002 | ............. A61L 15/24 |
| WO | WO 02-34304 | 5/2002 |
| WO | WO0234304 * 5/2002 | ............. A61L 15/32 |
| WO | WO 03-080133 | 10/2003 |

* cited by examiner

HYDROGELS WITH RELEASE ELEMENT

CROSS REFERENCE TO RELATED APPLICATIONS

This application is a national stage filing under 35 U.S.C. 371 of PCT/US2009/057983, filed Sep. 23, 2009, which claims priority to U.S. Provisional Application No. 61/099,584, filed Sep. 24, 2008, the disclosures of which are incorporated by reference in their entirety herein.

BACKGROUND OF THE INVENTION

Hydrocolloid adhesive compositions that are formed as dressings have been known for many years. Typically, these compositions comprise a blend of a polymer matrix, such as a rubbery elastomer like polyisobutylene, in combination with one or more water-soluble or water-swellable hydrocolloids, such as a dry powdered mixture of pectin, gelatin and carboxymethylcellulose. The adhesive composition is usually coated on at least one surface of a water-insoluble film to form a relatively thick, heavy dressing.

Commercially available examples of hydrocolloid dressings include "DUODERM" and "DUODERM EXTRATHIN" dressing (a product of Convatec; Squibb and Sons, Inc., Princeton, N.J.; 3M TEGADERM Hydrocolloid dressing (a product of 3M Company, St. Paul, Minn.); RESTORE dressing (a product of Hollister, Inc., Libertyville, Ill.); and COMFEEL dressing (a product of Coloplast International, Espergaerde, Denmark). See, also, U.S. Pat. Nos. 4,909,244; 5,447,492; and 5,106,629.

The TEGADERM Hydrocolloid dressing has a thin, adhesive coated polymeric backing extending beyond the edges of the absorbent hydrocolloid pad to form a border that will adhere to the skin and provide a barrier to outside contamination as well as keep wound fluid contained providing for a longer wear time as described in U.S. Pat. Nos. 6,436,432 and 6,264,976. A carrier frame surrounds the perimeter of the dressing, providing sufficient support (e.g. rigidity) to the backing to facilitate handling of the dressing during application to a wound.

Several contoured hydrocolloid adhesives used as medical dressings are described in U.S. Pat. Nos. 4,867,742; 5,133,821 (a process for making by an in-line process a contoured hydrocolloid adhesive dressing); U.S. Pat. No. 7,217,853 (dressing or patch with a tapered edge); U.S Patent Application Publication No. 2003/0125680; and EP Patent No. 0919211 A2. Despite these advances, a need remains for conformable dressings, particularly in an island dressing format.

SUMMARY OF THE INVENTION

The invention provides an adhesive hydrogel island dressing and delivery system that facilitates removal of a release liner from the adhesive hydrogel dressing during application and subsequently during removal from a patient. An adhesive hydrogel pad is provided with a release element along at least a portion of the edge of the hydrogel pad proximate the area that the hydrogel pad and release liner separate during liner removal. The release element disrupts the shear force that would otherwise occur in removing the release liner from the dressing. Disruption of shear force minimizes damage to the dressing (e.g., separation of the adhesive hydrogel from the backing layer or irreversible distortion of the dressing) during application of the dressing as well as assists in removal of the dressing from a patient.

In one embodiment, an island dressing is provided, comprising a backing that comprises a first major surface; an adhesive located on the first major surface of the backing; a hydrogel island pad proximate the first major surface of the backing, wherein the hydrogel comprises less than 45% water; and a release liner; wherein at least a portion of the edge of the hydrogel pad contains a release element proximate the area that the hydrogel pad and release liner separate during liner removal.

In another embodiment, an island dressing is provided, comprising a backing that comprises a first major surface; an adhesive located on the first major surface of the backing; a hydrogel island pad proximate the first major surface of the backing; and a release liner; wherein at least a portion of the edge of the hydrogel pad contains a release element proximate the area that the hydrogel pad and release liner separate during liner removal; and wherein the average maximum peel force to initiate separation of a one-inch wide hydrogel pad without a release element from a release liner is at least 25% greater than the average maximum peel force of the hydrogel pad with a release element from the release liner, when measured by the T-peel Test Method performed after conditioning the island dressing for one week at 50 degrees C.

In another embodiment, an island dressing is provided, comprising a backing that comprises a first major surface; an adhesive located on the first major surface of the backing; an adhesive hydrogel island pad proximate the first major surface of the backing; and a release liner; wherein at least a portion of the edge of the hydrogel pad contains a release element proximate the area that the hydrogel pad and release liner separate during liner removal and such substrate extends beyond the perimeter of the hydrogel and is affixed to the backing layer.

As used herein "hydrogel," and "hydrophilic gel" refers to a continuous phase of a hydrophilic polymer that is capable of swelling on contact with water and other hydrophilic swelling agents. The term is used regardless of the state of hydration. Useful hydrogels will absorb at least 40% by weight based on the hydrogel's weight in an anhydrous state. Hydrogels are hydrophilic polymers characterized by their hydrophilicity (i.e., capable of absorbing large amounts of fluid such as wound exudate). The hydrogels are typically transparent or translucent, regardless of their degree of hydration. Hydrogels are generally distinguishable from hydrocolloids, which typically comprise a hydrophobic matrix that contains dispersed hydrophilic particles.

These and various other advantages and features characterizing the invention are pointed out with particularity in the claims annexed hereto and forming a part hereof. However, for a better understanding of the invention, its advantages, and objects obtained by its use, reference should be made to the accompanying drawings and descriptive matter, in which preferred embodiments of the invention are illustrated and described.

BRIEF DESCRIPTION OF THE DRAWINGS

The invention will be further described with reference to the drawings, wherein corresponding reference characters indicate corresponding parts throughout the several views, and wherein:

FIG. 3b is a cross sectional view of the dressing of FIG. 3a.

FIG. 5b is cross sectional view of the dressing in FIG. 5a.

Figure 1:
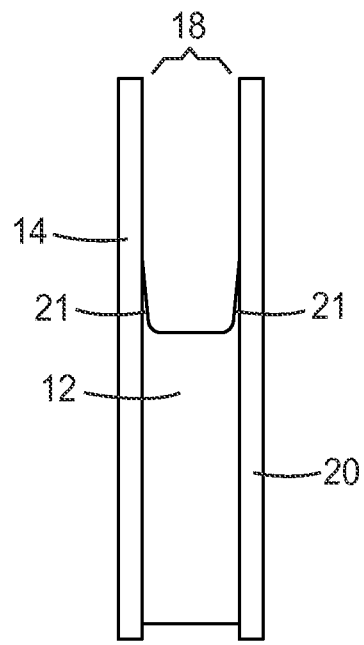
FIG. 1 is an exemplary enlarged side cross-sectional view of the adhesive hydrogel after shrinkage.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF PREFERRED EMBODIMENTS

The present invention is directed to an adhesive hydrogel dressing as well as to methods of applying the dressing to a patient, and removing the dressing from a patient. The dressing generally comprises an adhesive hydrogel pad, a backing layer, and an adhesive layer on the backing layer facing the hydrogel pad. The adhesive layer and backing layer form a perimeter around the hydrogel pad and hold the hydrogel pad in place on a surface. The perimeter formed by the adhesive layer and backing layer keeps the hydrogel pad properly positioned, and also helps maintain a sterile environment around the application surface.

The adhesive layer and backing layer are typically extremely thin, and generally very flexible. If the adhesive layer and backing layer are not properly supported during application they can easily fold over and adhere to themselves, preventing proper application over a surface. The adhesive layer and backing layer are optionally supported by a removable carrier attached to the top face of the backing layer. A release liner is provided to contact the adhesive and the adhesive hydrogel pad. Both the release liner and conformable backing layer coated with the adhesive extend beyond the edges of the hydrogel pad.

The adhesive hydrogel composition is integral with at least a portion of the hydrogel pad's edge having a release element adhered the edge of the hydrogel proximate the area that the hydrogel pad and release liner separate during liner removal. In some cases the release element extends beyond the edge of the hydrogel pad and may or may not adhere to the backing layer as well. The release element overcomes the problems with poor or inconsistent liner release that can occur with low modulus, highly conformable adhesive hydrogel compositions, such as those described herein. While not being bound by theory, the hydrogel compositions, after aging under low humidity conditions, can exhibit liner lock-up. Liner lock-up is generally considered the inability to remove the release liner without damaging or irreversibly distorting the dressing, which can result in dressing application failures.

Liner lock-up of the hydrogel pad on the release liner can occur for at least two reasons. First, the hydrogel composition, upon exposure to aging conditions (e.g., at least one week at less than 50% relative humidity at room temperature) will lose volatile components, such as water. The loss of volatile components results in shrinkage of the hydrogel composition, thereby generating a concave meniscus of the hydrogel bridging the backing layer and release liner, as shown in FIG. 1.

Second, the hydrogel composition typically has residual elasticity with an elastic recovery or shrinkage. In some embodiments, the hydrogel compositions comprise internal stress forces that have built through processing of the hydrogel compositions to form, for example, a pad construction of the hydrogel. After processing, these internal stresses cause the hydrogel compositions to experience shrinkage as the internal stresses act as a force causing elastic recovery of the hydrogel.

The effect of both moisture removal and internal stresses can separately, or in combination, affect meniscus formation. The volume movement or shrinkage of the hydrogel composition may be governed similarly to laminar flow of a viscous fluid under Poiseuille's law. Poiseuille's law is the physical law concerning the voluminal laminar stationary flow F of an incompressible uniform viscous liquid (i.e., a Newtonian fluid) through a cylindrical tube with constant circular cross-section.

Per Poiseuille's law, the volume movement is related to the radius of the tube the fluid is flowing to the fourth power. The elastic recovery of the hydrogel composition may behave similarly, considering the elastic recovery forces to follow the same relation as a pressure differential in Poiseuille's law. The release element acts to mechanically disrupt this force by reduction or elimination of adhesion of the adhesive hydrogel to the liner at certain locations, or by constricting the elastic nature of the adhesive hydrogel. This mechanical disruption results in substantially reduced peel forces upon initiation of release liner removal.

Typically, hydrogels suitable for use in the dressings described herein comprise less than 45% water, more preferably less than 30% by weight water, and most preferably less than 20% by weight water, based on the total weight of the hydrogel composition.

For example, the adhesive hydrogel composition can comprise a hydrogel comprising about 10% water at 50% relative humidity (RH) and 22° C. and about 6% water at 36% RH and 22° C. Under about 0% RH and 22° C. aging conditions, the moisture or water content of the hydrogel can drop below 3% by wt. At these moisture levels, the hydrogel modulus increases and the hydrogel's peel adhesion increases in relation to typical release liners. This increase in modulus and peel adhesion, when combined with hydrogels of significant thickness (such as thicknesses greater than 40 mils, preferably greater than 60 mils), will cause the release liner to change from peel removal to a shear removal, thereby dramatically altering (e.g., increasing) the force necessary to remove the liner.

The likeliness of a hydrogel composition to form this meniscus bridging the liner and backing can be assessed by a relatively simple method. With a hydrogel composition between two release liners, one on each side, several samples can be cut in the downweb and crossweb directions precisely using a cutting die, for example, a 3.8 cm by 5.1 cm die. The sample can be gently removed from the two liners and attached to a surface, preferably a shelf, along one of the narrower 3.8 cm dimension of the hydrogel. Approx 0.5 cm can contact the surface, leaving the remaining 4.5 cm to dangle downward, untouched by any surface. After 24 hours, the sample can be measured for width at the lowest point.

If the width remains unchanged, (i.e., the width is 3.8 cm) the sample has experienced 0% shrinkage. Correspondingly, if the hydrogel is now 1.9 cm wide, it has experienced 50% shrinkage. The samples can also be preweighed and post weighed to determine if they have gained or lost water or other volatiles. A sample which has not changed weight but has experienced shrinkage is likely due to residual elastic recovery forces within the hydrogel. The conditions can also be varied with respect to humidity and temperature to effect meniscal formation of the hydrogel.

Hydrogels as described herein typically experience shrinkage levels of at least 10%, and more often 40% depending on hydrogel processing, the calendaring gap used in manufacturing, and moisture levels. Typically higher moisture levels in the hydrogel result in low elastic recovery shrinkage but higher volatile shrinkage under low humidity conditions. Since process conditions can be difficult to achieve that minimize both shrinkage forces, the incorporation of the release element on a portion of the hydrogel pad provides a solution to address potential liner lock-up using these compositions.

Figure 2:
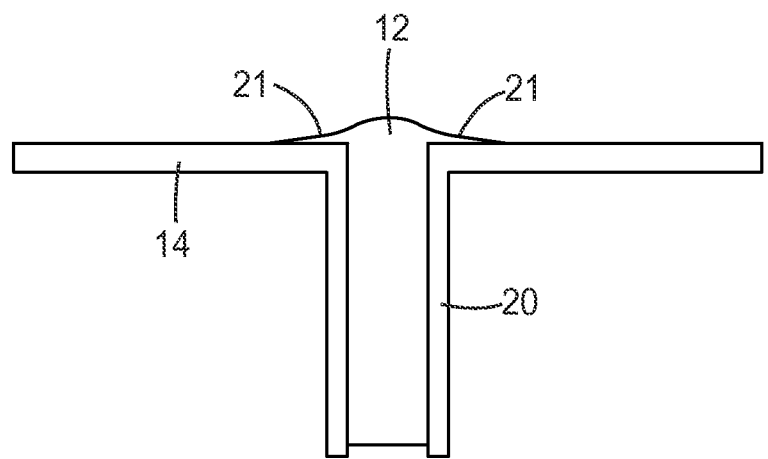
FIG. 2 is an exemplary enlarged side cross-sectional view of the adhesive hydrogel during peel.

FIGS. 1 and 2 schematically illustrate the difference in hydrogel characteristics in a hydrogel composition that lacks a release element on at least a portion of the edge. FIG. 1 depicts a hydrogel pad 12 between release liner 20 and backing layer 14 (coated with an adhesive) after contraction of the hydrogel in the center as the hydrogel pad 12 is exposed to aging conditions. The hydrogel pad 12 forms a meniscus 18 with extensions 21 of the hydrogel pad 12 along the surface of both the release liner 20 and the backing layer 14 (coated with an adhesive). The extensions 21 facilitate the hydrogel pad 12 entering a shear mode as the release liner 20 and backing layer 14 are pulled apart from each other in a T-peel fashion as depicted in FIG. 2.

FIGS. 3-6 depict preferred embodiments of the hydrogel pad dressing and delivery system designated in its entirety by the reference numeral 10. The dressing 10 includes a hydrogel pad 12 located proximate the center of the dressing 10. Although hydrogel pad 12 is shown as proximate the center of dressing 10 and as having a oval-like shape, it can take any appropriate shape and/or can be located off-center on the dressing 10 as desired. Hydrogel pad 12 typically contains an antimicrobial agent, described further below. The hydrogel pad 12 is covered by an adhesive layer on a backing layer 14 that extends out to the perimeter 15 of the dressing 10. The backing layer 14 is typically extremely thin, flexible, and either transparent or translucent, allowing the hydrogel pad 12 to be viewed through it.

In FIGS. 3-6, an optional adhesive laminate 17 (as viewed through transparent backing layer 14) is also provided. One type of adhesive laminate that can be used is described in U.S. Pat. No. 5,088,483. The adhesive laminate 17 can be a laminate of an adhesive and a substrate such as a film or fabric.

As shown in FIGS. 3-6, adhesive laminate 17 is affixed to the backing layer 14 after the bottom face of the backing layer 14 is coated with a pressure sensitive adhesive, with the adhesive laminate 17 exposed so that the adhesive laminate 17 will adhere to the skin or other surface to which the dressing 10 is applied. The adhesive laminate 17 may be provided on the backing layer 14 in any pattern.

Figure 6:
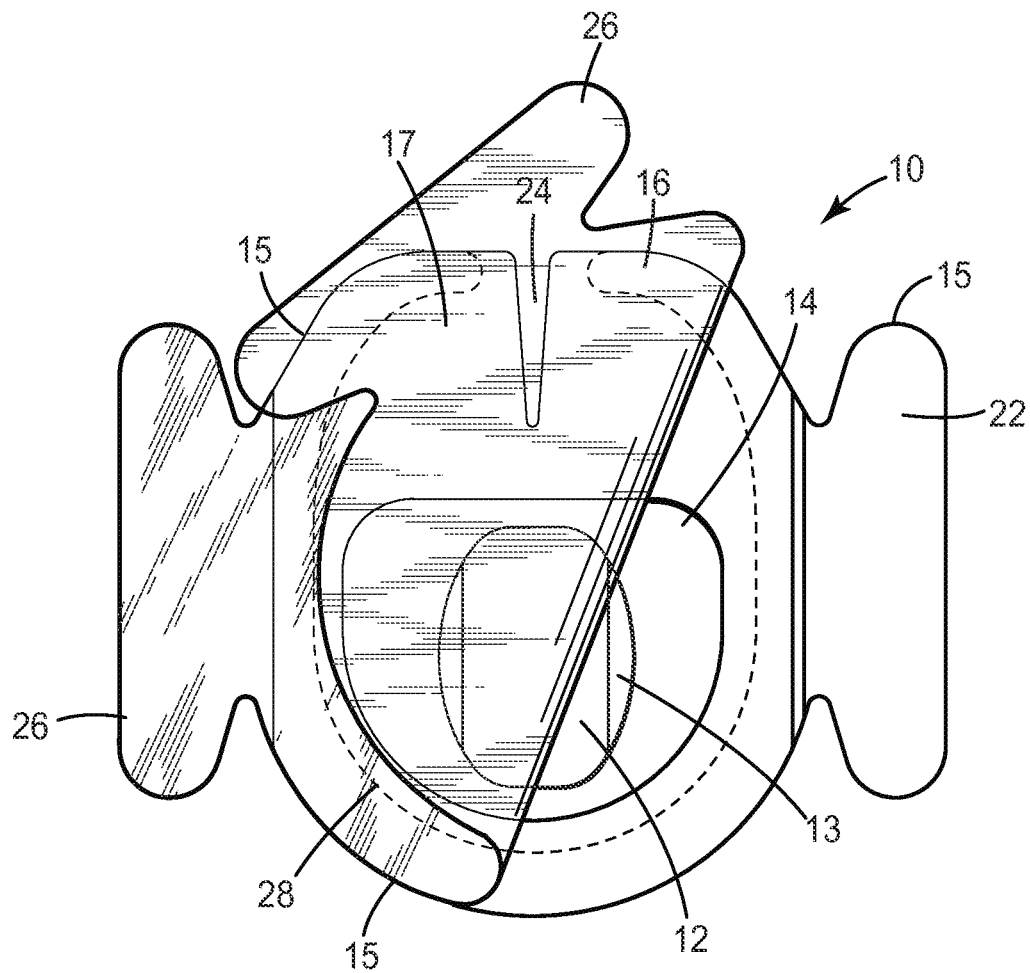
FIG. 6 is an exemplary enlarged bottom view of an adhesive hydrogel dressing with release element.

Adhesive laminate 17 is applied to at least a portion of backing layer 14 on the same side of backing layer 14 as the adhesive layer 19 (as shown in FIG. 6). A release liner 20 covers the adhesive layer 19, the hydrogel pad 12, and the adhesive laminate 17. Release liner 20 is optionally die cut or may optionally extend beyond the adhesive coated face of backing layer 14 to enable easy removal by the user.

The adhesive laminate 17 may provide some reinforcing and conformability properties to the backing material. This adhesive reinforcement may be a film/adhesive laminate, such as HYTREL (DuPont, Wilmington, Del.) film and tackified acrylate adhesive such as a copolymer of iso-octyl acrylate, acrylic acid and FORAL 85 (a triglyceryl ester of reduced abietic acid, commercially available from Hercules Chemical Co., Wilmington, Del.) tackifier. Another adhesive laminate 17 may be a fabric/adhesive laminate. Examples of nonwoven fabric/adhesive laminates include embodiments such as disclosed in U.S. Pat. No. 4,366,814 and available commercially as STERI-STRIP," (3M Company, St. Paul, Minn.) elastic skin closure, a nonwoven elastomeric melt blown web of thermoplastic elastomeric small diameter fibers, or CEREX (Monsanto, St. Louis, Miss.) spun bonded nylon and adhesive. Woven fabric/adhesive laminates include embodiments such as cotton cloth laminated to a rubber based adhesive.

A carrier layer 16 is optionally positioned over the backing layer 14. The carrier layer 16 can be a single piece of material, such as a polymeric film, or can be two or more distinct pieces. In the embodiments of FIGS. 3-6, the carrier layer 16 comprises at least one portion that extends beyond the edge of the backing layer 14 of the dressing 10 to form a tab 22. The tab 22 can be held during positioning of the dressing 10.

The carrier layer 16 extends along substantially the entire periphery of the backing layer 14 and forms a window 28 exposing a portion of the backing layer 14 overlying the hydrogel pad 12 with the backing layer 14 sandwiched between the carrier layer 16 and hydrogel pad 12. As used herein, the term "sandwiched" means that one layer is intermediate or between two other layers. For example, the backing layer 14 may be considered an intermediate layer between the carrier layer 16 and the hydrogel pad 12, and thus is "sandwiched" between the carrier layer 16 and hydrogel pad 12.

A window 28 may be cut (e.g., controlled depth die cut) from a carrier blank to form a carrier layer 16 having a window exposing a portion of the top surface of the backing layer 14. The cut or window portion of the carrier blank may be either removed during manufacturing or by the consumer. Removal during manufacturing eliminates one step in the delivery process for previously known window style dressings and reduces the waste stream at the consumer level. Some customers, however, prefer that the portion of the carrier covering window 28 remains intact until the dressing 10 reaches the consumer.

In the embodiment shown in FIGS. 3-6, the carrier layer 16 has an opening such that the frame extends slightly less than completely around the perimeter of the backing layer 14. The opening allows the dressing to be placed over catheters or other devices while still attached to the frame to increase the ease of handling of backing layer 14.

In preferred embodiments, a notch 24 may be provided in dressing 10. In applications using the dressings with other devices, such as a percutaneous device, the notch 24 allows the dressing 10 to conform around bulky parts of the other device, or may conform around portions of the device that exit the area of dressing application, such as a catheter line.

Referring again to FIGS. 3-6, the dressing 10 typically includes a release liner 20, also having a tab 26. The release liner 20 covers the surface of the dressing 10 applied to the patient, generally making contact with the hydrogel pad 12, the periphery of the adhesive laminate 17, and the adhesive 19. The release liner 20 typically remains attached to dressing 10 until a user is ready to apply the dressing. The release liner 20 may be a single piece or multiple piece release liner, and may be part of or laminated to the package (not shown) containing the dressing, or merely enclosed along with the dressing within the package.

Pressure sensitive adhesive layer 19 is generally provided on one major surface of the backing layer 14 in order to make it adhesive, and a low adhesion coating (low adhesion backsize or LAB) may be provided on the other major surface of the backing layer 14 on the side that comes in contact with the carrier layer 16. The low adhesion coating reduces the need to change the dressing 10 due to unwanted dressing removal when other tapes or devices are placed on the dressing 10 and removed, and reduces the surface friction of the dressing 10 on linen or other fabrics, thereby offering additional protection against the accidental removal of dressing 10. A description of a low adhesion backing material suitable for use with the present invention can be found in U.S. Pat. Nos. 5,531,855 and 6,264,976, which are compatible with a heat seal bond described below, and are incorporated herein in their entirety.

The hydrogel pad 12 of dressing 10 is sometimes referred to as an "island pad" because the backing layer 14 extends substantially beyond the hydrogel pad 12, typically beyond the entire edge of the hydrogel pad 12. As used herein, an island pad also includes constructions wherein the backing layer extends partially beyond the hydrogel pad 12, for example, at least 50% of the periphery of the hydrogel pad 12. For example, the length and width of the hydrogel pad 12 can be 3 cm by 7 cm, while a backing for this pad can be 10 cm by 15.5 cm.

The carrier layer 16 is preferably attached to the second major surface of the backing layer 14 (over the low adhesion backing). The bond between the carrier layer 16 and the backing layer 14 is stronger than the bond between the adhesive layer 19, adhesive laminate 17, or hydrogel pad 12, and the release liner 20 so that the backing layer 14 remains attached to the carrier layer 16 when the release liner 20 is removed from the dressing 10. Once the release liner 20 and dressing 10 are separated, only the carrier layer 16 and hydrogel pad 12 provide significant rigidity to the backing layer 14.

Various other embodiments are contemplated from the aspects shown in FIGS. 3-6. For example, the backing layer 14 can be multiple films or coatings without diverging from the invention or deviating from the meaning of the term "film" as used herein. Similarly, the hydrogel pad 12 can include multiple sub-layers, including films, webs, sheets, etc. Also, additional layers and films of other materials can be added between the materials described herein.

The hydrogel pad 12 can comprise a hydrogel composition as described further below having a thickness of at least 2 mils, more preferably 40 mils, and most preferably 50 mils and including thicknesses up to 500 mils. The backing layer 14 can comprise a transparent elastic polymeric film (e.g., urethane) having a thickness in the range of 0.02 to 0.2 mm and most preferably 0.021-0.051 mm. As shown in FIG. 5, the thickness of the hydrogel pad 12 relative to the other layers of the dressing 10 can create an air gap 11 around the periphery of the hydrogel pad 12.

Figure 3A:
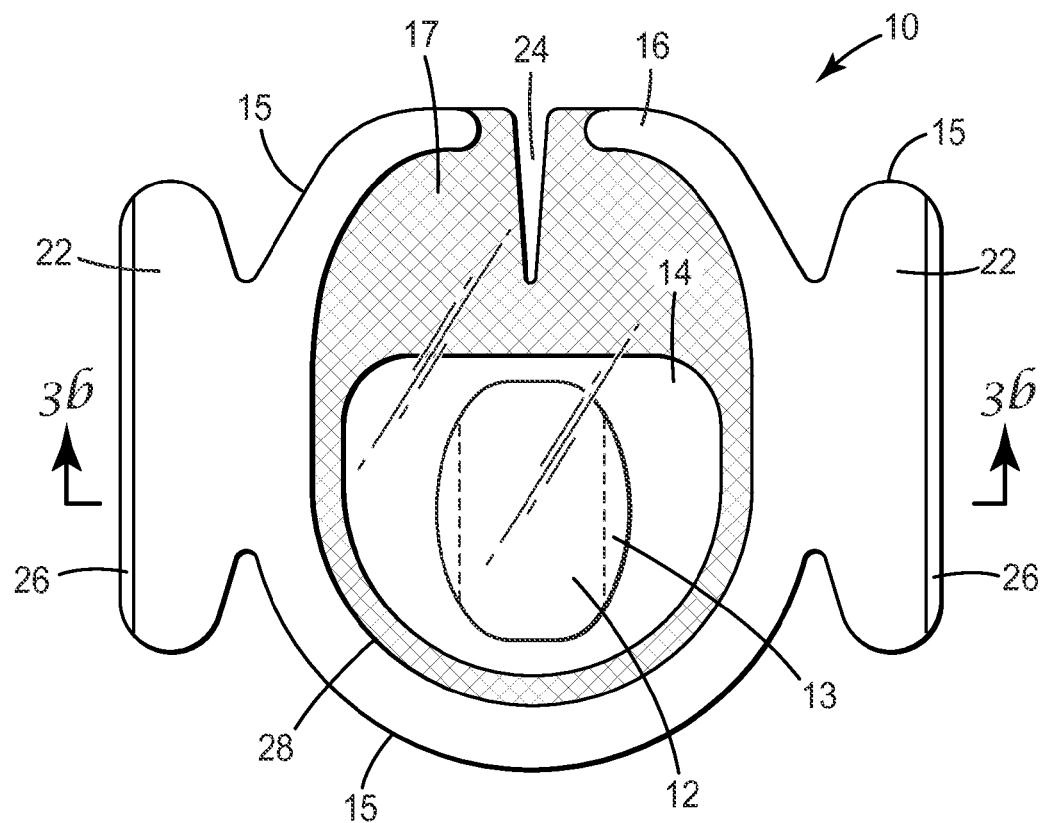
FIG. 3a is an exemplary top view of an adhesive hydrogel dressing with release element.
Figure 3B:
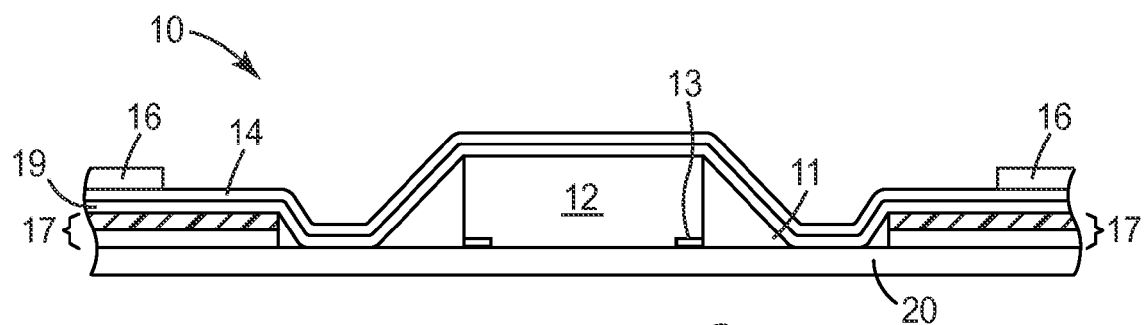
Figure 4:
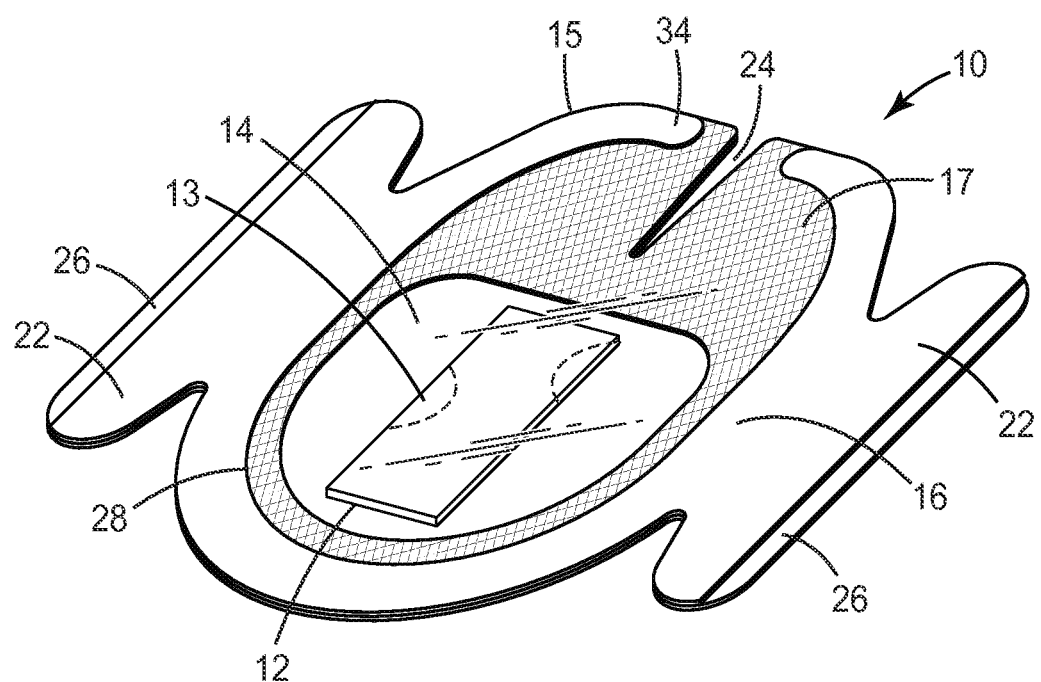
FIG. 4 is an exemplary top view of an adhesive hydrogel dressing with release element.
Figure 5A:
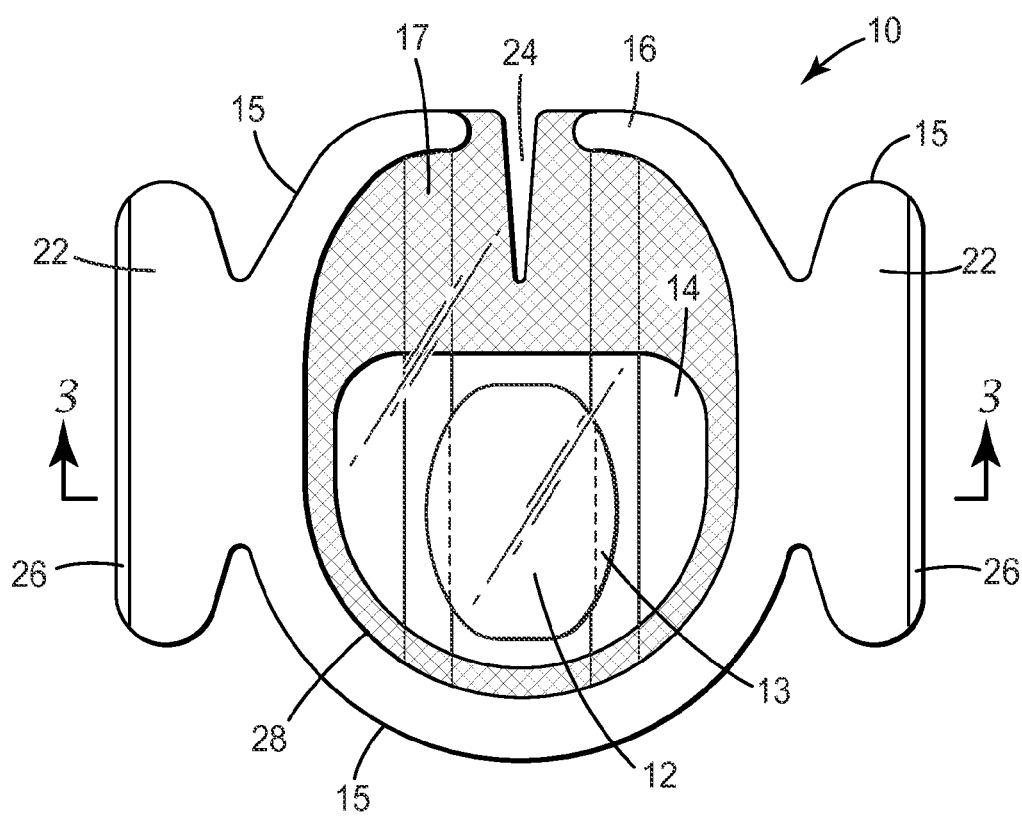
FIG. 5a is an exemplary top view of an adhesive hydrogel dressing with release element.
Figure 5B:
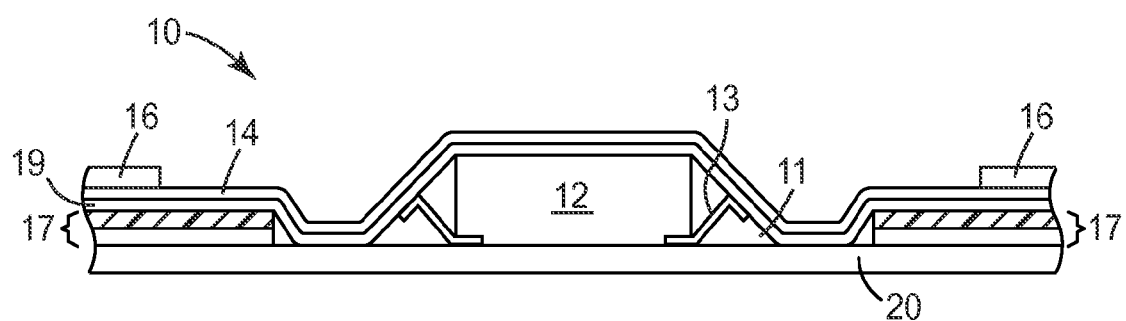

As shown in FIGS. 3-6, a release element 13 is provided that can be configured on at least a portion of the edge of the hydrogel pad 12 proximate the area that the hydrogel pad 12 and release liner 20 separate during liner removal. The release element 13 can take the shape of a strip or semicircle along the periphery of the hydrogel pad along the point where liner peel is initiated as shown in FIGS. 3a, 3b, 6 and 7e. The release element 13 can also take the shape of tabs as shown in FIG. 4 or as elongated strips that extend past the hydrogel pad 12 to come into contact with the backing layer 14 as shown in FIGS. 5a and 5b. Although FIGS. 3-6 describe shapes that may be preferred, the release element may take any shape desired on at least a portion of the edge of the hydrogel pad 12 proximate the area that the hydrogel pad and release liner separate during liner removal, thus minimizing or otherwise affecting the formation or legs of a meniscus 18 with extensions 21 as shown in FIGS. 1-2. FIG. 6 depicts the embodiment shown in FIGS. 5a and 5b from the bottom side. In this depiction the release liner 20 has been pulled back to show the skin facing surface of the hydrogel pad 12 and the release element 13.

The release element 13 may cover the entire periphery of the hydrogel pad 12 in a frame-like construction. Preferably the release element 13 may cover at least 1% of the periphery of the hydrogel pad 12 proximate the area that the hydrogel pad and release liner separate during liner removal. In some embodiments the release element 13 may remain adhered to the release liner 20 after liner removal instead of remaining with the hydrogel pad 12 or the dressing 10.

The release element 13 at the liner peel interface minimizes the peel force necessary to initiate peel of the hydrogel pad 12 from the release liner 20 or prevents liner removal difficulty. In configurations where the release element 13 remains with hydrogel pad 12, the release element also minimizes the peel force necessary to remove the hydrogel pad 12 and dressing 10 from a patient. Difficulty in peel removal of the liner from the hydrogel pad 12 can encompass both liner lock-up (the inability to remove the liner without damaging or irreversibly distorting the dressing), and reduced ease in removing the liner where the average maximum peel force of a hydrogel pad without the release element 13 is increased greater than 25% relative to a similar construction of a hydrogel pad 12 with a release element 13, and measured during liner removal by the T-peel test described below.

FIGS. 7 a-e depict an exemplary method of applying and removing the dressing 10 of FIG. 3 to a patient. In FIGS. 7a-e, the hydrogel dressing 10 is depicted as a dressing covering a percutaneous device, such as an intravenous catheter (IV). The dressing 10 is typically applied to a patient by first cleaning the application area and inserting the IV. The release liner 20 is then removed from the dressing, exposing the bottom of the hydrogel pad 12, the adhesive laminate 17 and the backing layer 14 (coated with adhesive layer 19), as shown in FIG. 7a. Once removed from release liner 20, hydrogel pad 12 is brought in contact with the catheter site, covering catheter device 30, and then the edges of the dressing 10 are gently and smoothly pressed against the patient, thereby bringing the exposed adhesive perimeter of the backing layer 14 and the adhesive laminate 17 in contact with the patient, as shown in FIG. 7b. The catheter line 32 exits the dressing 10 at the notch 24. This configuration aids in placement of hydrogel pad 12 to optimize secural of the lumen and hub of a catheter.

Figure 7A:
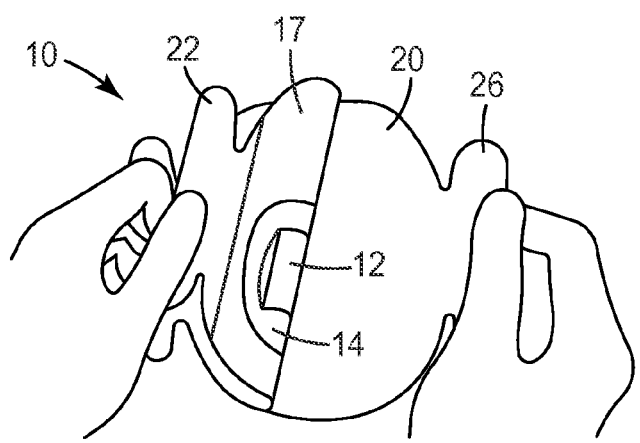
FIGS. 7a-7e is an exemplary depiction of a method of applying and removing the dressing of FIG. 3a to a patient.
Figure 7B:
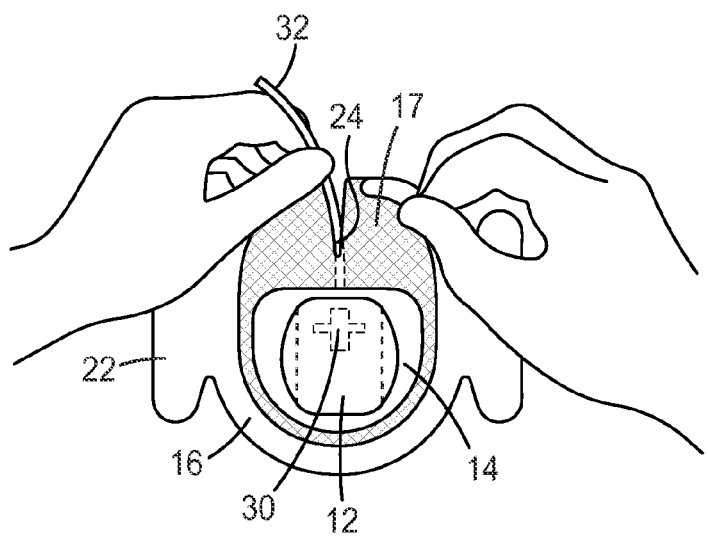
Figure 7C:
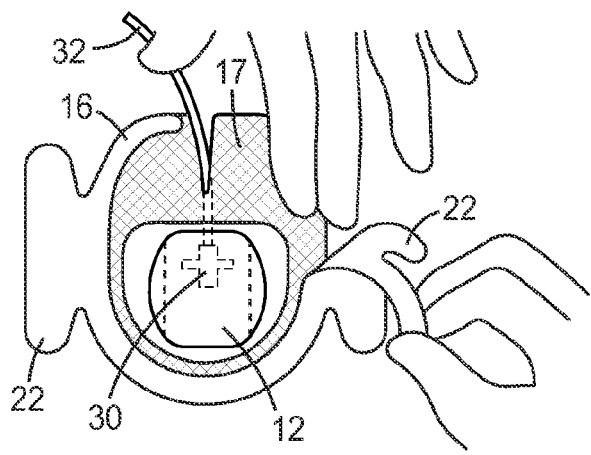
Figure 7D:
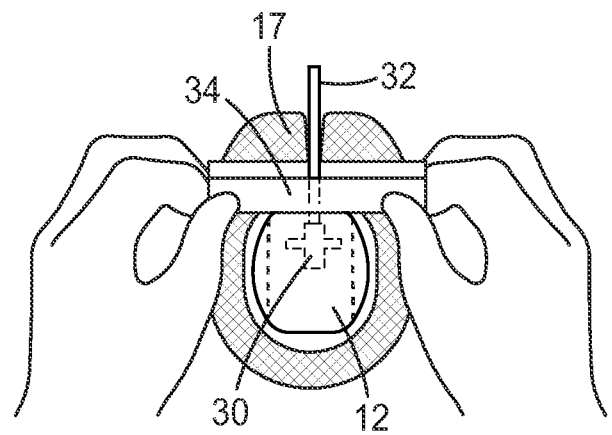
Figure 7E:
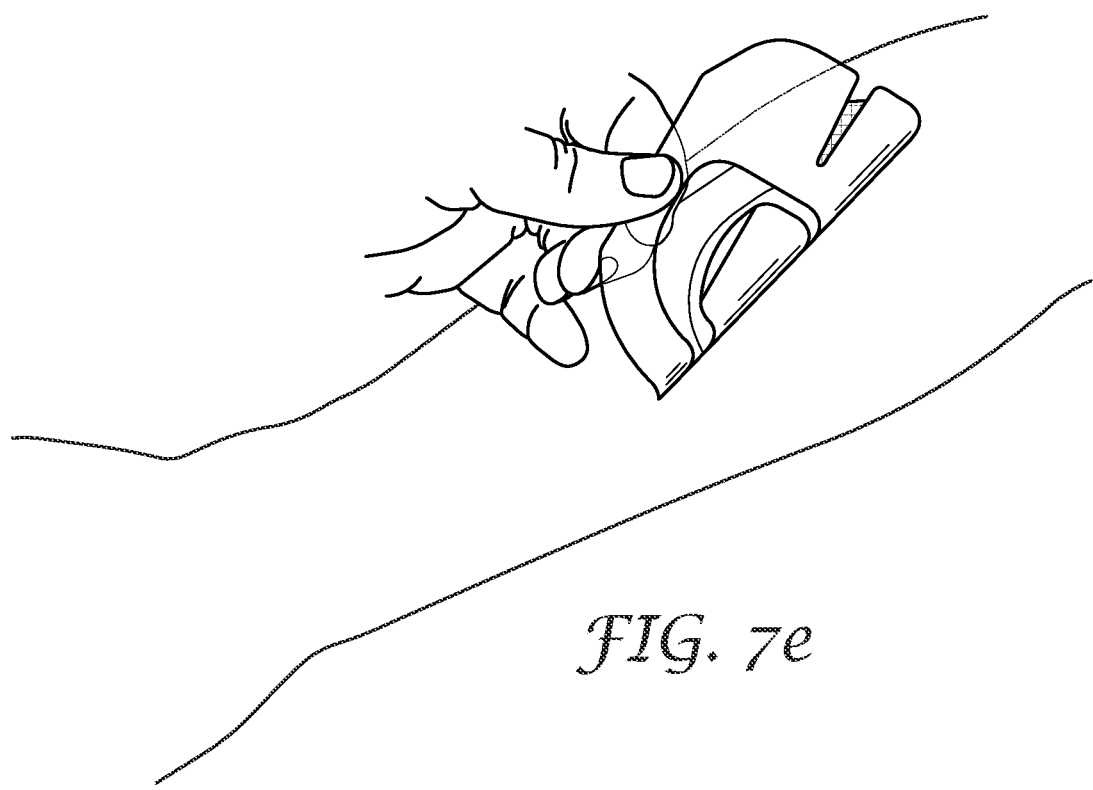

After the dressing 10 is properly in position and adhered to a patient's skin, the carrier layer 16 can be removed, as shown in FIG. 7c. Generally removal of carrier layer 16 is accomplished by grasping the carrier layer at area 34 and using a peeling motion toward the edges of the dressing 10 to remove the carrier layer 16. After application of the dressing 10, optional tapes 34 may be placed over the dressing 10 to cover catheter line 32 exiting dressing 10 at notch 24. The tapes 34 may be provided with the dressing 10 may be supplied separately.

During removal of the dressing, the release element may also facilitate removal of the dressing from the patient and/or catheter as it facilitates the removal of the adhesive hydrogel from the skin and/or catheter. The release element may be non-adherent to skin, be less adherent to skin than the hydrogel or have the same adherence to skin as the hydrogel.

The layers and materials discussed above are further described in detail below.

Hydrogel Materials

Suitable hydrogel compositions include, for example, a natural hydrogel, such as pectin, gelatin, or carboxymethylcellulose (CMC) (Aqualon Corp., Wilmington, Del.), a semi-synthetic hydrogel, such as cross-linked carboxymethylcellulose (X4ink CMC) (e.g. Ac-Di-Sol; FMC Corp., Philadelphia, Pa.), a synthetic hydrogel, such as cross-linked polyacrylic acid (PAA) (e.g., CARBOPOL™ No. 974P; B.F. Goodrich, Brecksville, Ohio), or a combination thereof.

In most embodiments, the hydrogel dressing comprises a swellable, crosslinked poly(N-vinyl lactam), a swelling agent and a modifying polymer present in an amount sufficient to form a cohesive, pressure-sensitive adhesive composition as described further in Applicants co-pending application, U.S. Patent Application Publication No. 2004-0247655-A1. The amount of swelling agent to be mixed with the crosslinked swellable poly(N-vinyl lactam) can range from about 50 to about 90 weight percent of the composition. Consequently, exclusive of any biocompatible and/or therapeutic and/or ionically-conductive materials to be added to the composition, the weight percent of the swellable poly(N-vinyl lactam) can be from about 10 to about 50 weight percent. When the poly(N-vinyl lactam) is poly(N-vinyl pyrrolidone), the weight percent of poly(N-vinyl pyrrolidone) can range from about 15 to about 45 percent. In particular embodiments, the poly (N-vinyl pyrrolidone) can range from about 18 percent to about 35 percent.

In most embodiments, the adhesive composition of the present invention comprises a swellable, poly(N-vinyl lactam) that is radiation-crosslinked, typically while the lactam is in a solid form. In other embodiments, the poly (N-vinyl) lactam is crosslinked by free-radical polymerization, either in bulk or in solution, of a precursor containing an N-vinyl lactam monomer, optionally other monomers, and a crosslinking compound as described in U.S. Pat. No. 4,931,282. Poly(N-vinyl lactam) useful in the present invention can be provided in any form susceptible to being crosslinked such as the solid forms described in U.S. Pat. Nos. 4,931,282, 5,225,473 and 5,389,376. Typically, the poly(N-vinyl lactam) is a homopolymer of N-vinyl-2-pyrrolidone.

After exposure to ionizing radiation, poly(N-vinyl lactam) can have a Swelling Capacity in water of at least about 15, typically at least about 30, and often at least about 40 as described in U.S. Pat. No. 5,409,966, which is incorporated herein by reference. Poly(N-vinyl lactam) in any solid form may be crosslinked for use when subjected to ionizing radiation from a high-energy source.

The modifying polymer is present in the adhesive composition to maintain and/or increase cohesiveness while reducing adhesiveness. When added with the swelling agent, the modifying polymer becomes solubilized or suspended in the swelling agent. Typically, the modifying polymer will form a viscous solution or viscous gel when combined with the swelling agent in a ratio of modifying polymer to swelling agent of 1:9.

The choice of swelling agent typically will determine the appropriate modifying polymer to accomplish a reduction in adhesion while maintaining or improving cohesion of the adhesive composition. Modifying polymers that are poorly solubilized in one swelling agent may be highly swollen in a different swelling agent for use in the present invention. In some embodiments, examples of suitable modifying swellable polymers include, but are not limited to, polysaccharides, polysaccharide derivatives, acrylates, acrylate derivates, cellulose, cellulose derivatives, and combinations thereof.

In particular embodiments, modifying swellable polymers for use in the present invention are hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing.

The amount of modifying polymer can range up to about 50 weight percent of the composition. Consequently, exclusive of any biocompatible and/or therapeutic and/or ionically-conductive materials to be added to the composition, the weight percent of the modifying polymer can be from about 0.1 to about 40 weight percent. When the modifying polymer is hydroxypropyl guar, the weight percent of hydroxypropyl guar can range from about 1 to about 20 percent.

The hydrogel composition also comprises a swelling agent which can swell both the crosslinked poly(N-vinyl lactam) polymer and the modifying polymer, and which is biocompatible with human skin. Nonlimiting examples of swelling agents useful to swell the poly(N-vinyl lactam) include monohydric alcohols (e.g., ethanol and isopropanol), polyhydric alcohols, (e.g., ethylene glycol, propylene glycol, polyethylene glycol (Molecular Weight between 200 and 600) and glycerin), ether alcohols (e.g., glycol ethers), other polyol swelling agents which do not cause skin irritation or toxic reaction, and water.

Depending on the ultimate use desired for the adhesive composition, non-volatile and/or volatile swelling agents may be used. One suitable swelling agent may comprise volatile swelling agent and non-volatile swelling agent, such as a mixture of glycerin or polyethylene glycol with water. In some embodiments, non-volatile swelling agents may be used by themselves such as, for example, glycerin or polyethylene glycol. Likewise, volatile swelling agents such as water may be used by themselves in the compositions of the invention. For this invention, "essentially non-volatile" means that a swelling agent as used in the present invention will render the adhesive polymer, such as radiated poly(N-vinyl lactam), sufficiently cohesive and pressure sensitive adhesive, such that less than ten percent (10%) of a given volume of nonvolatile swelling agent evaporates after exposure to processing or storage conditions.

The swelling agent can be added in an amount ranging from about 50 to about 90 weight percent of the adhesive composition and preferably from about 60 to about 80 weight percent. In some embodiments, glycerin and polyethylene glycol are chosen to be the essentially non-volatile swelling agent. Both glycerin and polyethylene glycol can comprise up to 100 weight percent of the swelling agent.

Hydrogel pad 12 is useful for containing a number of substances, optionally including antimicrobial agents, drugs for transdermal drug delivery, chemical indicators to monitor hormones or other substances in a patient, etc.

Antimicrobial Agents

The hydrogel composition can deliver an antimicrobial agent to the skin, reducing the likeliness of an infection to a percutaneous device or to treat infections of the skin or wounds. In most embodiments, the antimicrobial agent is added in levels up to 10% by weight of the total composition.

There are numerous biologically active materials, which include antimicrobial agents. Examples of antimicrobial agents include parachlorometaxylenol; triclosan; chlorhexidine and its salts such as chlorhexidine gluconate, poly hexamethylene biguanide and its salts such as poly hexamethylene biguanidine chloride, iodine, idodophors; fatty acid monoesters; poly-n-vinyl pyrrolidone-iodophors; silver oxide, silver and its salts, peroxides (e.g. hydrogen peroxide), antibiotics (e.g. neomycin, bacitracin, and polymixin B). Other suitable antimicrobial agents are those listed in U.S. Patent Application Publication No. 2004-0247655-A1.

A method of preparing a pressure-sensitive adhesive composition of the present invention comprises mixing crosslinked poly(N-vinyl lactam) with a swelling agent and a modifying polymer, and other additives in a solvent which may be somewhat volatile at or above ambient temperatures. Typically, the swelling agent, modifying polymer, and other additives, such as antimicrobial agents, are in essentially unirradiated form. Examples of suitable volatile solvents include water, ethanol, methanol, and isopropanol. A quantity of the resulting suspension is then cast onto a surface of a substrate, such as a release liner or a backing material and then stored. The volatile solvent is evaporated by heating such as by the application of microwave energy, infrared energy, or by convective air flow or the like, in order to form a cohesive, pressure-sensitive adhesive composition on the substrate. Often, a drying oven heated to about 65 degree C. may be employed for the evaporation step. A product release liner can optionally be laminated over the exposed surface of the composition to protect it from contamination.

Backing Materials

Suitable backing materials for backing layer 14 include, for example, nonwoven fibrous webs, woven fibrous webs, knits, films and other familiar backing materials. The backing materials are typically translucent or transparent polymeric elastic films. The backing can be a high moisture vapor permeable film backing U.S. Pat. No. 3,645,835 describes methods of making such films and methods for testing their permeability.

The backing advantageously should transmit moisture vapor at a rate equal to or greater than human skin. In some embodiments, the adhesive coated backing layer transmits moisture vapor at a rate of at least 300 g/m$^2$/24 hrs/37° C./100-10% RH, frequently at least 700 g/m$^2$/24 hrs/37° C./100-10% RH, and most typically at least 2000 g/m$^2$/24 hrs/37° C./100-10% RH using the inverted cup method.

The backing layer 14 is generally conformable to anatomical surfaces. As such, when the backing layer 14 is applied to an anatomical surface, it conforms to the surface even when the surface is moved. The backing layer 14 is also conformable to animal anatomical joints. When the joint is flexed and then returned to its unflexed position, the backing layer 14 can be made such that it stretches to accommodate the flexion of the joint, but is resilient enough to continue to conform to the joint when the joint is returned to its unflexed condition.

A description of this characteristic of backing layers 14 for use with the present invention can be found in U.S. Pat. Nos. 5,088,483 and 5,160,315. Specific suitable backing materials are elastomeric polyurethane, co-polyester, or polyether block amide films. These films combine the desirable properties of resiliency, high moisture vapor permeability, and transparency found in backings.

Carrier Layer

The material used to form the carrier layer 16 is generally substantially more rigid than the backing layer 14 to prevent the backing layer 14 from improperly wrinkling during application to a patient. The carrier layer 16 can be heat-sealable to the backing layer 14 with or without a low adhesion coating described above. In general, the carrier layer materials can include, but are not limited to, polyethylene/vinyl acetate copolymer-coated papers and polyester films. One example of a suitable carrier layer material is a polyethylene/vinyl acetate copolymer coated super calendared Kraft paper (1-80BKG-157 PE; LOPAREX of Willowbrook, Ill.).

The carrier layer 16 can include perforations to aid in separating portions of the carrier layer 16 after application of the dressing 10 in a patient. Spacing and shape of the perforations are adjusted to give a carrier layer with relatively easy to tear performance on removal of the carrier layer from the applied dressing. The perforations may be shaped in accordance with any of the accepted perforation patterns including linear, angled, Y-shaped, V-shaped, dual-angled offset, sinusoidal, etc.

Adhesive Layer

Various pressure sensitive adhesives can be used to form adhesive layer 19 on the backing layer 14 to make it adhesive. The pressure sensitive adhesive is usually reasonably skin compatible and "hypoallergenic", such as the acrylate copolymers described in U.S. Pat. No. RE 24,906. Particularly useful is a 97:3 iso-octyl acrylate:acrylamide copolymer, as is a 70:15:15 isooctyl acrylate:ethyleneoxide acrylate:acrylic acid terpolymer which is described in U.S. Pat. No. 4,737,410. Additional useful adhesives are described in U.S. Pat. Nos. 3,389,827, 4,112,213, 4,310,509, and 4,323,557. Inclusion of medicaments or antimicrobial agents in the adhesive is also contemplated, as described in U.S. Pat. Nos. 4,310,509 and 4,323,557.

The adhesive layer 19 can be coated on the backing layer 14 by a variety of processes, including, direct coating, lamination, and hot lamination.

Release Liner

Release liner 20 suitable for use as described herein can be made of kraft papers, polyethylene, polypropylene, polyester or composites of any of these materials. The films are preferably coated with release agents such as fluorochemicals or silicones. For example, U.S. Pat. No. 4,472,480 describes low surface energy perfluorochemical liners. The liners are papers, polyolefin films, or polyester films coated with silicone release materials. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films commercially available from H. P. Smith Co. and fluoropolymer coated polyester films commercially available from 3M Company under the brand "ScotchPak™" release liners.

Release Element

Release element 13 suitable for use as described herein can be made of any substrate that does not fully diffuse or absorb into the hydrogel. The release element maintains sufficient separateness from the hydrogel pad to disrupt the peel force necessary to initiate the peel of the hydrogel pad from the release liner or prevent liner removal difficulty. For example, the release element may be comprised of a continuous or perforated film; a knitted fabric; a woven or non-woven fabric; a nonwoven fibrous web; woven fibrous web; knits; films; porous; apertured or perforated film; nonporous; non-apertured or non-perforated film; nylon; woven threads; scrims; foams; discontinuous or continuous coatings; polymeric materials delivered in solution; emulsion; latex or dispersion; particles including non-adhesive or low adhesive particles; and other familiar backing materials. The release element may also include an adhesive that aids in adhesion of the release element to the hydrogel or the backing of the dressing. In cases where the release element is incorporated into the dressing such that it acts to constrict the elastic nature of the hydrogel, the adhesive layer of the release element may be exposed to the release liner during application, and therefore, the patient's skin during use.

Methods of Manufacturing

Incorporation of the release element into the dressing as described herein is readily achieved by those skilled in the arts of converting and lamination. For example, if the release element is located on the hydrogel pad only, the release element can be laminated as strips onto a web of the adhesive hydrogel. Individual adhesive hydrogel pads can then be cut from the web and placed onto the backing such that the adhesive gel and release element are oriented and located as desired on the dressing. The release element laminated to the adhesive hydrogel may be straight or have a wave like pattern. If the release element is in a wave like pattern, the release element may be located at least partially on the hydrogel pad after cutting the web as exemplified in FIG. 4.

In examples where the release element is in contact with both the adhesive hydrogel pad and the adhesive of the backing material, the release element is laminated to the backing and a portion of the adhesive hydrogel after the adhesive hydrogel pad is placed on the backing. As familiar to those skilled in the art, this lamination can be achieved in variety of ways. For example, the release element may be laminated as a strip to the release liner in the desired location on the release liner prior to lamination of the release liner to the backing layer containing the adhesive hydrogel pad. In examples where the release element is comprised of discrete particles, or a polymer or material that is coated from a solution, emulsion or dispersion, the release element can be coated, sprayed or otherwise deposited onto the adhesive hydrogel using a variety of pattern coating techniques known to those skilled in the art such as patterned roll coating, mask coating or edge coating of the hydrogel web material.

EXAMPLES

T-Peel Test Method

T-Peel measurement is conducted using a Zwick tensile tester, model Z005 (available from Zwick USA, Kennesaw, Ga.) or equivalent with the jaw speed set at 6 inches (15.24 cm) per minute and the gauge at 2 inches (5.1 cm). Data is collected for the maximum (peak) peel force in ounce-force units produced during the T-peel. Unless otherwise stated, the standard test liner is a LOPAREX 2 mil (51 micrometer) PET liner with 164Z release coating, (available from LOPAREX of Willowbrook, Ill.). Unless otherwise stated the standard conditioning for a test sample is drying in an oven at 50° C. for a minimum of 1 week.

For each sample the release liner is lightly folded (not creased) just prior to and parallel to the hydrogel edge to facilitate the 180° peel. While holding the sample flat, the product liner is clamped in the top jaw of the tensile tester and the remaining layers of the dressing in the bottom jaw. The hydrogel patch is aligned with the lower and upper jaws so that the peel would reach the edge of the hydrogel patch evenly. The sample is left "loose" between the jaws to avoid separating the liner from the hydrogel prior to taking the measurement.

Example 1

Two strips of 1" wide MICROPORE (3M Company, St. Paul, Minn.) tape were laminated to the surface of a hydrophilic adhesive gel web such that the MICROPORE strips were separated by approximately 1.25" of exposed gel, and the adhesive side of the MICROPORE tape faced the hydrophilic adhesive gel. The hydrophilic adhesive gel used for this example is disclosed in U.S. Patent Application Publication No. 2004-0247655-A1. An oval shaped die (1.5"×2") was then used to cut out a shape such that the edges of the gel along the 1.5" width of the gel contained approximately ⅛" of MICROPORE tape. The oval shaped gel was then trimmed on each side of the long dimension of the oval to shorten the total length of the hydrogel pad to approximately 1.6". FIGS. 3a and 3b generally depict this construction. This gel pad was then laminated to the adhesive side of a commercially available 3M TEGADERM 1655 IV Transparent Film dressing (3M Company, St. Paul, Minn.) such that the MICROPORE tape strips (3M Company, St. Paul, Minn.) faced the product release liner. The product release liner was replaced with a 2 mil clear polyester liner with a 4400/0000 release coating (commercially available from LOPAREX). Numerous samples were made this way and aged for two weeks at various temperatures (i.e., approximately 25° C., 40° C., and 49° C.).

After the two weeks of aging, the samples were allowed to cool to room temperature, then cut in half such that the liner could be removed from each side of the dressing and the maximum peel force recorded. The maximum peel force during liner removal from the gel portion of the product was then tested using a 180 degree T-peel test conducted at 6 inches per minute on a Zwick/Roell Z005 (commercially available from Zwick USA, Kennesaw, Ga.). The thickness of the gel pad at the leading edge of peel was measured using a caliper and was recorded. The average of three or four maximum peel force values and gel thickness values from samples from each side of the dressing and their standard deviations are summarized in Table 1.

TABLE 1

Summary of results from Example 1

| Example | Aging Temperature (° C.) | Side 1 Gel Thickness (mm) | Side 1 Maximum Peel Force (oz/sample) | Side 2 Gel Thickness (mm) | Side 2 Maximum Peel Force (oz/sample) |
| --- | --- | --- | --- | --- | --- |
| 1 | 25 | 1.1 +/− 0.1 | 3.2 +/− 0.1 | 1.7 +/− 0.2 | 3.1 +/− 0.3 |
| 1 | 40 | 1.1 +/− 0.1 | 5.5 +/− 0.6 | 1.7 +/− 0.1 | 5.7 +/− 0.9 |
| 1 | 49 | 1.2 +/− 0.1 | 6.3 +/− 1.0 | 1.8 +/− 0.1 | 7.0 +/− 1.2 |

Example 2

Control

Samples were prepared in the same manner as Example 1 except no MICROPORE strips were laminated to the hydrophilic adhesive gel prior to constructing the samples. The average of three or four maximum peel force values and gel thickness values from samples from each side of the dressing and their standard deviations are summarized in Table 2.

TABLE 2

Summary of results from Example 2

| Example | Aging Temperature (° C.) | Side 1 Gel Thickness (mm) | Side 1 Maximum Peel Force (oz/sample) | Side 2 Gel Thickness (mm) | Side 2 Maximum Peel Force (oz/sample) |
|---|---|---|---|---|---|
| 2 | 25 | 1.1 +/− 0.1 | 3.8 +/− 1.7 | 1.7 +/− 0.1 | 14.6 +/− 7.0 |
| 2 | 40 | 1.2 +/− 0.3 | 5.9 +/− 0.6 | 1.8 +/− 0.1 | >18.4 +/− 9.8* |
| 2 | 49 | 1.1 +/− 0.1 | 6.0 +/− 0.8 | 1.8 +/− 0.1 | >28.9 +/− 5.3** |

*The gel of 1 of 4 samples did not release from liner during maximum peel force testing.
**The gel of 3 of 4 samples did not release from the liner during maximum peel force testing.

Example 3

Samples were prepared in the same manner as Example 1 except strips of film/adhesive laminate cut from the 3M TEGADERM on a Roll #16004 product (3M Company, St. Paul, Minn.) (adhesive side facing the gel) were laminated to the hydrophilic adhesive gel, instead of MICROPORE strips. The carrier on the 3M TEGADERM on a Roll product was removed after the lamination of the strips. The average of three or four maximum peel force values and gel thickness values from samples from each side of the dressing and their standard deviations are summarized in Table 3.

TABLE 3

Summary of results from Example 3

| Example | Aging Temperature (° C.) | Side 1 Gel Thickness (mm) | Side 1 Maximum Peel Force (oz/sample) | Side 2 Gel Thickness (mm) | Side 2 Maximum Peel Force (oz/sample) |
|---|---|---|---|---|---|
| 3 | 25 | 1.2 +/− 0.1 | 3.5 +/− 1.0 | 1.9 +/− 0.1 | 3.0 +/− 0.6 |
| 3 | 40 | 1.1 +/− 0.1 | 5.4 +/− 0.4 | 1.9 +/− 0.1 | 6.8 +/− 0.9 |
| 3 | 49 | 1.1 +/− 0.2 | 6.0 +/− 0.7 | 1.9 +/− 0.1 | 6.5 +/− 0.8 |

Example 4

Samples were prepared in the same manner as Example 1 except strips of polyvinyl alcohol (PVA) film (0.0254 mm thick, NP#25, Aicello North America, (North Vancouver, British Columbia) were laminated to the hydrophilic adhesive gel instead of MICROPORE strips. Samples from Example 4 were only aged at 49° C. The average of three maximum peel force values and gel thickness values from samples from each side of the dressing and their standard deviations are summarized in Table 4.

TABLE 4

Summary of results from Example 4

| Example | Aging Temperature (° C.) | Side 1 Gel Thickness (mm) | Side 1 Maximum Peel Force (oz/sample) | Side 2 Gel Thickness (mm) | Side 2 Maximum Peel Force (oz/sample) |
|---|---|---|---|---|---|
| 4 | 49 | 1.0 +/- 0.1 | 5.8 +/- 0.7 | 1.8 +/- 0.2 | 6.6 +/- 1.9 |

Example 5

A 3 cm×4 cm rectangular piece of the hydrophilic adhesive gel from Example 1 was laminated to the adhesive side of a 3M TEGADERM 1626W Transparent Film dressing (3M Company, St. Paul, Minn.). Approximately 1.25 cm wide strips of film/adhesive laminate were prepared similar to the film/adhesive combination described in Example 2 of U.S. Pat. No. 5,849,325. The strips were placed along the edges of the gel (film side facing gel) such that the film was also attached to the film adhesive backing (see construction shown in FIGS. 5a and 5b). The product liner was replaced with a 3 mil Polyethylene liner from LOPAREX that was coated with a release chemistry identified as 164Z. The samples were aged for 11 days at room temperature or 49° C. After aging, the samples were prepared in a similar fashion to that described in Example 1. The gel thickness was measure at the edge of the gel. The average of two or three maximum peel force values and gel thickness values from samples from each side of the dressing and their standard deviations are summarized in Table 5.

TABLE 5

Summary of results from Example 5

| Example | Aging Temperature (° C.) | Side 1 Gel Thickness (mm) | Side 1 Maximum Peel Force (oz/sample) | Side 2 Gel Thickness (mm) | Side 2 Maximum Peel Force (oz/sample) |
|---|---|---|---|---|---|
| 5 | 25 | 1.7 +/- 0.1 | 5.0 +/- 1.3 | 2.0 +/- 0.1 | 4.9 +/- 0.1 |
| 5 | 49 | 1.7 +/- 0.2 | 6.4 +/- 1.3 | 2.0 +/- 0.1 | 5.1 +/- 0.6 |

Example 6

The rheological properties of the gel were measured as a function of drying temperature and time using a TA Instruments' ARES rheometer (Texas Instruments, New Castle, Del.). Samples were dried at 48.9° C. The shear measurements were taken at 24° C. and a frequency range from 0.1 to 500 rad/second. The adhesive gel sample was a 25 mm diameter circle with a thickness of 1.6 mm. The results for the dynamic shear viscosity are shown in Table 6a. The results of the storage shear modulus (G'), and the loss shear modulus (G") are shown in Table 6b.

TABLE 6a

Change in viscosity (poise) with drying time at different shear rates.

| | Viscosity (Poise) | | |
|---|---|---|---|
| Drying time (days) | 1 rad/sec | 10 rad/sec | 100 rad/sec |
| 0 | 171000 | 28660 | 6299 |
| 1 | 215900 | 37350 | 8727 |
| 7 | 266300 | 50040 | 13330 |

TABLE 6b

The change of the shear modulus (G') and the loss shear modulus as a function of drying time and shear rate.

| | G' and G" as a function of shear rate | | | | | |
|---|---|---|---|---|---|---|
| Drying time | 1 rad/sec | | 10 rad/sec | | 100 rad/sec | |
| (days) | G' | G" | G' | G" | G' | G" |
| 0 | 150000 | 53000 | 245000 | 125000 | 500000 | 380000 |
| 1 | 200000 | 72000 | 325000 | 160000 | 650000 | 550000 |
| 7 | 235000 | 98000 | 420000 | 243000 | 910000 | 930000 |

Example 7

A solution of 3% HPG water was made from 97.0 gm DI Water, 3.0 gm Jaguar HP-120, (commercially available from Rhodia, Cranbury, N.J.) and 0.02 gm D&C Red 30. This solution was sponge applied to the front edge of the hydrogel pad, on the release liner side. This solution was allowed to dry for 5 min. Then a release liner was applied over the construction. Twenty samples of each were prepared on 2 mil PET liner coated with LOPAREX 7300 silicone release and 2 mil PET liner coated with LOPAREX 164Z. All samples were placed in 50 C oven for 2 weeks and T-peel tested for max peel with the peel initializing at the HPG coated edge.

A graph of the results of this Example 7 is reported below. The following data are averages of 20 T-peel trials using two different liners, LOPAREX 7300 and LOPAREX 164Z, both were on 2 mil PET.

TABLE 7

Summary of results from Example 7

| Construction | Ave Max peel for 20 samples (oz) | Maximum peel (oz) | Failure Rate (# greater than 20 oz) |
|---|---|---|---|
| 7300 with HPG Coated Gel | 3.07 | 8.34 | 0 |
| 164Z with HPG Coated Gel | 4.5 | 7.14 | 0 |
| 7300 uncoated Gel | 7.92 | 17.13 | 0 |
| 164Z uncoated Gel | 11.76 | 22.95 | 1 in 20 |

As various changes could be made in the above constructions, compositions and methods without departing from the scope of the invention as defined in the claims, it is intended that all matter contained in the above description or shown in the accompanying drawings be interpreted as illustrative and not in a limiting sense. The Examples described in this application are illustrative of the possibilities of varying the type, quantity and ratio of composition as well as the methods for making formulations of the present invention. The complete disclosures of all patents, patent applications, and publications recited herein are incorporated by reference, as if individually incorporated by reference.

What is claimed is:

1. An island dressing comprising
a backing that comprises a first major surface;
adhesive located on the first major surface of the backing;
a release liner in contact with a portion of the adhesive on the first major surface of the backing;
a hydrogel island pad positioned between the first major surface of the backing and the release liner; and
two release elements separated from each other on the hydrogel island pad, wherein each release element is positioned along a portion of a periphery of the hydrogel island pad, wherein at least a portion of each release element is sandwiched between the hydrogel island pad and the release liner;
wherein the release liner contacts a portion of the hydrogel island pad between the two release elements.

2. The island dressing of claim 1, wherein the release element contacts at least a portion of the backing.

3. The island dressing of claim 1, wherein the release element contacts at least a portion of the backing and is attached to at least a portion of the backing.

4. The island dressing of claim 1, wherein the release element comprises a layer of adhesive on the skin facing surface of the release element that exhibits less tack than the adhesive located on the first major surface of the backing.

5. The island dressing of claim 1, wherein the hydrogel island pad is attached to the adhesive on the first major surface of the backing.

6. The island dressing of claim 1, further comprising a carrier releasably attached to a second major surface of the backing.

7. The island dressing of claim 1, further comprising an adhesive laminate applied to at least a portion of the adhesive on the first major surface of the backing, wherein the release liner covers the adhesive, the hydrogel island pad, and the adhesive laminate.

8. The island dressing of claim 1, wherein the average maximum peel force to initiate separation of an one-inch wide hydrogel pad and a release liner without the release element is at least 25% greater than the average maximum peel force of the hydrogel pad and the release liner with a release element, when measured by the T-peel Test Method performed after conditioning the island dressing for one week at 50° C.

9. The island dressing of claim 1, wherein the hydrogel pad comprises less than 45% water.

10. The island dressing of claim 1, wherein the release element is comprised of a polymer film, a porous non-woven fabric, or a porous knitted fabric.

11. The island dressing of claim 1, further comprising an antimicrobial agent.

12. The island dressing of claim 1, wherein each release element is a strip.

13. The island dressing of claim 1, wherein the hydrogel comprises
a first polymer comprising a cross-linked poly (N-vinyl) lactam;
a swelling agent; and
a second modifying polymer swellable in the swelling agent;
wherein the first polymer forms a pressure sensitive adhesive in the presence of the swelling agent; and
wherein the second modifying polymer and the swelling agent reduce the adhesiveness of the first polymer while at least maintaining the cohesion of the composition.

14. The island dressing of claim 13 wherein the poly (N-vinyl)lactam is selected from the group consisting of poly N-vinyl-2-pyrrolidone, poly N-vinyl-2-valerolactam, poly N-vinyl-2-caprolactam, and combinations thereof.

15. The island dressing of claim 13 wherein the swelling agent is selected from the group consisting of monohydric alcohols, polyhydric alcohols, glycerol, polyglycerols, sorbitol, polyhydric alcohol ethoxylates, methoxides of polyethylene glycol, methoxides of polyhydric alcohol ethoxylates, and combinations thereof.

16. The island dressing of claim 13 wherein the second modifying polymer comprises at least one of a polysaccharide, polysaccharide derivatives, acrylate, acrylate derivatives, cellulose, cellulose derivatives, and combinations thereof.

17. The island dressing of claim 13 wherein the second modifying polymer is selected from the group consisting of hydroxypropyl guar, guar gum, hydroxyethyl cellulose, hydroxypropyl cellulose, hydroxypropyl methylcellulose, polymeric quaternary ammonium salt of hydroxyethyl cellulose reacted with trialkyl ammonium substituted epoxide, copolymers of hydroxyethyl cellulose and diallyldimethyl ammonium chloride, and derivatives and combinations thereof.

18. The island dressing of claim 17 wherein first polymer is poly N-vinyl-2-pyrrolidone, the swelling agent is triglycerol and the antimicrobial agent is chlorhexidine gluconate.

* * * * *

UNITED STATES PATENT AND TRADEMARK OFFICE
CERTIFICATE OF CORRECTION

PATENT NO. : 9,457,123 B2
APPLICATION NO. : 13/119225
DATED : October 4, 2016
INVENTOR(S) : David Holm et al.

Page 1 of 1

It is certified that error appears in the above-identified patent and that said Letters Patent is hereby corrected as shown below:

In the Specification

Column 10
Line 13, delete "derivates," and insert -- derivatives, --, therefor.

Column 11
Line 15, delete "idodophors;" and insert -- iodophors; --, therefor.
Line 18, delete "polymixin" and insert -- polymyxin --, therefor.

Column 18
Line 49 (approx.), delete "50 C" and insert -- 50°C. --, therefor.

In the Claims

Column 20
Line 15 (approx.), in Claim 13, delete "poly (N-vinyl) lactam" and insert -- poly(N-vinyl lactam) --, therefor.
Line 26 (approx.), in Claim 14, delete "poly (N-vinyl)lactam" and insert -- poly(N-vinyl lactam) --, therefor.

Signed and Sealed this
Seventh Day of November, 2017

Joseph Matal
*Performing the Functions and Duties of the
Under Secretary of Commerce for Intellectual Property and
Director of the United States Patent and Trademark Office*